United States Patent [19]
Benedick

[11] Patent Number: 5,692,246
[45] Date of Patent: Dec. 2, 1997

[54] CHEST PILLOW CHEST PROTECTOR

[75] Inventor: Rose Marie Benedick, Dover, Pa.

[73] Assignees: Ray A. Benedick; Rose M. Benedick, both of Dover, Pa.

[21] Appl. No.: 653,797

[22] Filed: May 28, 1996

Related U.S. Application Data

[60] Provisional application No. 60/001,109 Jul. 13, 1995.

[51] Int. Cl.$^6$ .............. A41D 27/12; A41D 13/00
[52] U.S. Cl. .............. 2/463; 2/464; 2/455; 2/92; 5/630
[58] Field of Search .............. 2/455, 463, 464, 2/44, 92, 456, 459, 460, 466, 467, 46, 48, 51, 52, 69, 69.5; 5/630, 632, 643; 297/465; 11/488

[56] References Cited

U.S. PATENT DOCUMENTS

| | | | |
|---|---|---|---|
| 525,710 | 9/1894 | Keogh | 2/455 |
| 2,056,767 | 10/1936 | Blath | 5/630 |
| 2,266,886 | 12/1941 | MCoy | 2/465 X |
| 2,468,841 | 5/1949 | Siegel | 2/463 |
| 3,500,472 | 3/1970 | Castellani | 2/465 X |
| 3,550,159 | 12/1970 | Alarco | 2/463 |
| 3,941,404 | 3/1976 | Otaegui-Ugarte | 280/150 |
| 4,507,801 | 4/1985 | Kavanagh et al. | 2/465 X |
| 4,525,875 | 7/1985 | Tomczak | 2/2 |
| 4,829,613 | 5/1989 | Yon | 5/630 |
| 4,872,215 | 10/1989 | Sliger | 2/2 |
| 4,891,846 | 1/1990 | Sager et al. | 2/49 R |
| 4,993,076 | 2/1991 | Dierickx | 2/2 |
| 5,020,156 | 6/1991 | Neuhalfen | 2/2 |
| 5,245,706 | 9/1993 | Moschetti et al. | 2/2 |
| 5,329,636 | 7/1994 | Siddle | 2/463 |
| 5,363,523 | 11/1994 | Blackburn | 5/630 |

*Primary Examiner*—Jeanette E. Chapman
*Attorney, Agent, or Firm*—Walter C. Farley

[57] ABSTRACT

A chest pillow for use by a post-surgical patient has a flexible plate and padding surrounding and covering all sides and edges of the plate. A fabric cover surrounds and encloses the padding and the plate. Separable straps extend between upper and lower edges of the pillow, the straps having sufficient length to pass around the upper body of the patient, thereby to hold the pillow in a desired position, ready for use.

1 Claim, 3 Drawing Sheets

CHEST PILLOW CHEST PROTECTOR

CROSS-REFERENCE TO RELATED APPLICATION

This application is based on provisional application 60/001,109 filed Jul. 13, 1995.

FIELD OF THE INVENTION

This invention relates to a pillow which can be worn and held to a person's chest to provide protection and comfort, and particularly to reduce discomfort following surgery and in other circumstances.

BACKGROUND OF THE INVENTION

During recovery after certain kinds of surgery, a patient who has had an incision in the chest commonly needs to apply gentle pressure to his or her chest to reduce discomfort, for example, if it is necessary to cough. Coughing without such pressure is not only painful but it can be dangerous if the muscular spasm associated with coughing exerts forces on the incision. This danger is reduced if gentle, overall pressure can be applied to the chest.

It is also important for a patient to be able to protect the chest from such routine irritants as a seat belt in an automobile. If the patient is well enough to ride, or even drive, a conventional automobile, it is important for him or her to wear the conventional seat belt, but that belt can be annoying, uncomfortable or even harmful to an unprotected chest which has been surgically invaded.

It has been customary for a physician to recommend use of a small couch pillow or even a stuffed animal for this purpose. While some of these circumstances can be partially taken care of in the home with an ordinary bed or couch pillow, such pillows do not provide the support, uniformly distributed pressure and comfort required for all situations and, in addition, it is inconvenient and cumbersome to carry a pillow from the home into various outside situations, particularly if the patient is elderly.

SUMMARY OF THE INVENTION

Accordingly, an object of the present invention is to provide a pillow which is capable of being either carried or worn on a patient's body and which provides the various needs of a post surgical patient with a healing chest incision.

Briefly described, the invention comprises a chest pillow for use by a post-surgical patient having a flexible plate having a width and a height perpendicular to its thickness and to each other, said width and height approximating upper body width and rib cage height dimensions of a patient. Padding surrounds and covers all sides and edges of the plate. A fabric cover surrounds and encloses the padding, and separable straps extend between upper and lower edges of the pillow, the strap means having sufficient length to pass around the upper body of the patient, thereby to hold the pillow in a desired position so as to be available for use.

BRIEF DESCRIPTION OF THE DRAWINGS

In order to impart full understanding of the manner in which these and other objects are attained in accordance with the invention, a particularly advantageous embodiment thereof will be described with reference to the following drawings, which form a part of this disclosure, and wherein.

DESCRIPTION OF THE PREFERRED EMBODIMENT

Figure 1:
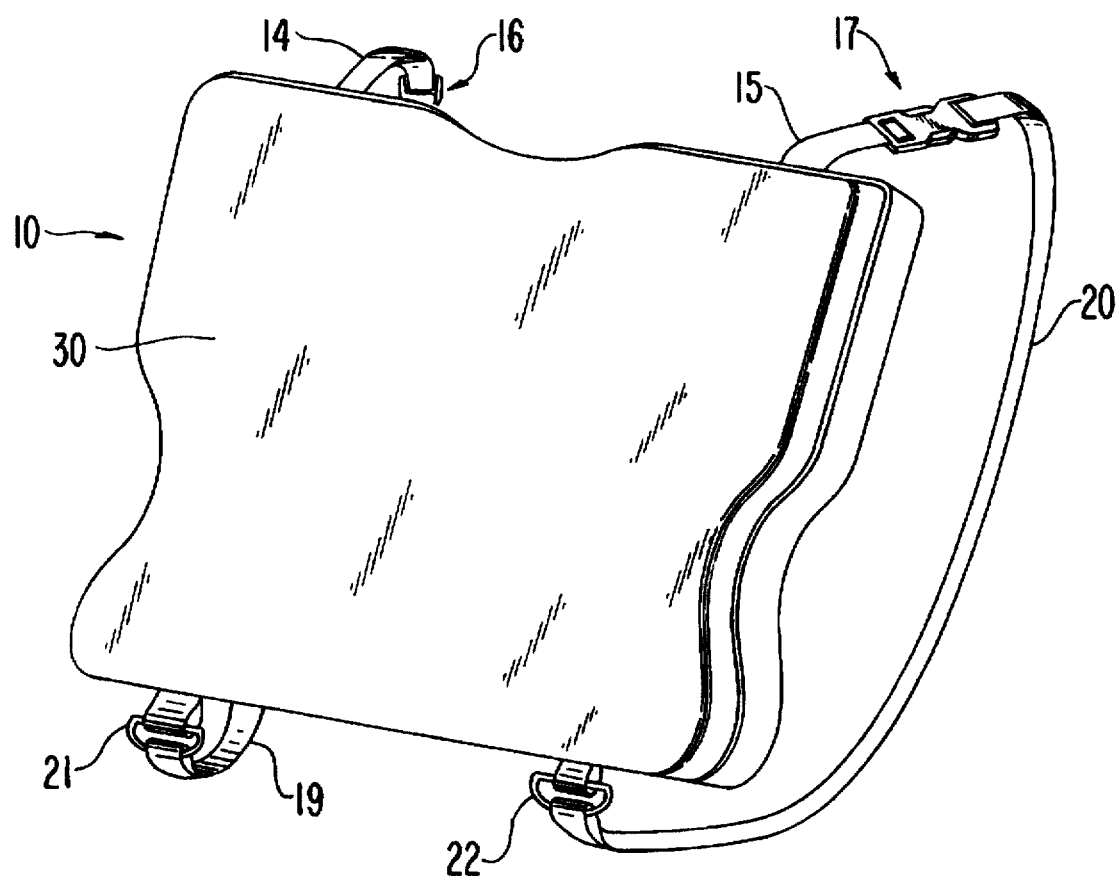
FIG. 1 is a perspective view of a chest pillow in accordance with the invention.
Figure 2:
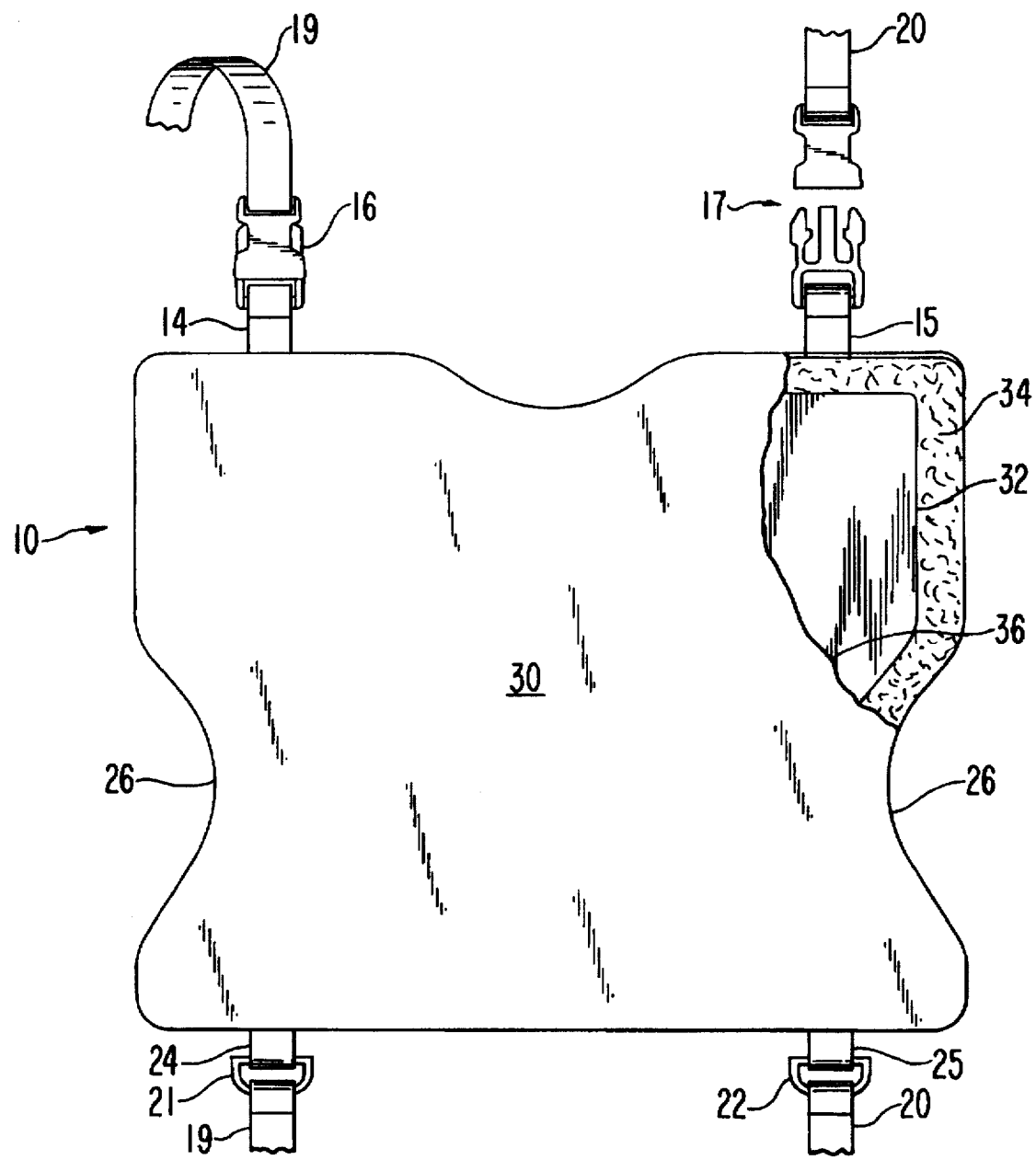
FIG. 2 is a front elevation, partly cut away, of the chest pillow of FIG. 1.

Referring now to the drawings, FIGS. 1 and 2 show a chest pillow in accordance with the invention indicated generally at 10. The pillow has a generally rectangular shape with an indentation 12 at an upper edge thereof to leave space for the chin and neck of a person using the pillow. As seen in the side elevation of FIG. 3, the pillow is to be worn or held against the chest and extends approximately from beneath the chin, or at the level of the clavicle, to the bottom of the rib cage, about 12 inches, although it will be recognized that this relationship will vary somewhat depending on the specific dimensions of the pillow and the size of the person for whom it is made. The pillow is about 3 inches thick and is about 13 inches wide.

On both sides of indentation 12, straps 14 and 15 are attached to upper edge of pillow 10, i.e., the edge which is uppermost when the pillow is in its normal orientation for use. The other end of each of straps 14 and 15 is attached to one side of a separable buckle 16 and 17, respectively. Buckles 16 and 17 are preferably of a type which is conventionally used on a parachute harness or on SCUBA equipment and is releasable with one hand by squeezing the sides of the buckle to release its latches. The other sides of the buckles are connected to further lengths of strap 19 and 20 which extend to the bottom of the pillow. Straps 19 and 20 are connected to conventional D rings 21 and 22 which pass through loops 24 and 25 attached to the pillow itself.

Straps 14 and 15 are rather short, on the order of 3 or 4 inches long, while straps 19 and 20 are longer than the vertical dimension of the pillow, allowing them to pass around the back of a person wearing the pillow so that it need not be manually held all of the time. Preferably, the buckles are identical and interchangeable so that the straps can be connected across the back, if the patient wishes, or can simply be looped around the shoulders without crossing.

Opposite side edges of the pillow are formed with indentations 26 to permit the user's arms to pass comfortably around the pillow to the front thereof, "front" in this context meaning a major surface 30 of the pillow which faces away from the person wearing it.

The interior structure of the pillow includes an inner, central plate 32 made of a flexible plastic material such as a high density polyethylene which has sufficient stiffness to maintain the shape of the pillow but which can bend to a considerable extent. It is desirable for the plate to be flexible enough so that the pillow can follow and bend with body motions without impeding them, the plate serving the primary purpose of giving the pillow its shape. Plate 32 has the same shape as the overall outline of the pillow but is smaller so that it can be padded on all sides and edges. Surrounding plate 32 is a layer of padding 34 such as polyester fiber to form a soft pad capable of conforming to the body shape of the user. Preferably, padding 34 is wrapped around plate 32 in a vertical direction to minimize the possibility of the plate slipping downwardly inside the pillow. Alternatively, the padding can be fastened or stitched through the plate to keep the padding and plate together.

The outside layer 36 of the pillow is made of a durable fabric which can be woven or knitted. Preferably, it is made with seams joining fabric panels at at least the bottom and top edges so that straps 14 and 15 and loops 24 and 25 can be sewn into the seams, holding them securely.

Figure 3:
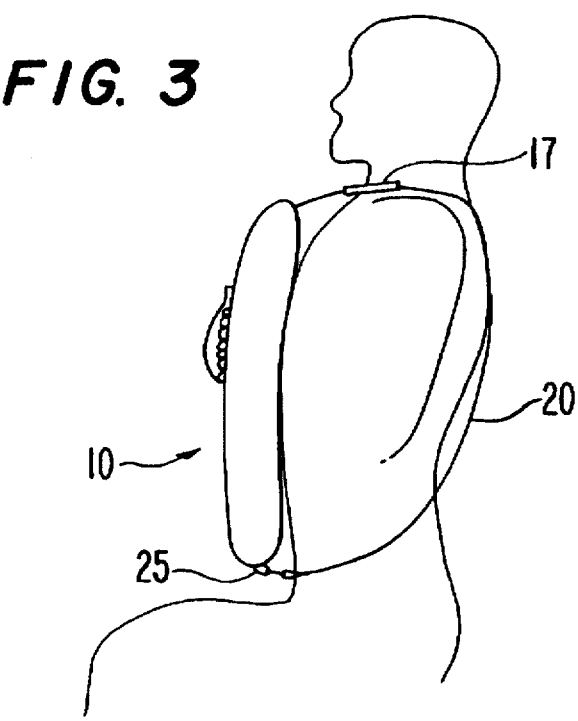
FIG. 3 is a side elevation of the pillow of FIGS. 1 and 2 in a typical position of use on a person.
Figure 4:
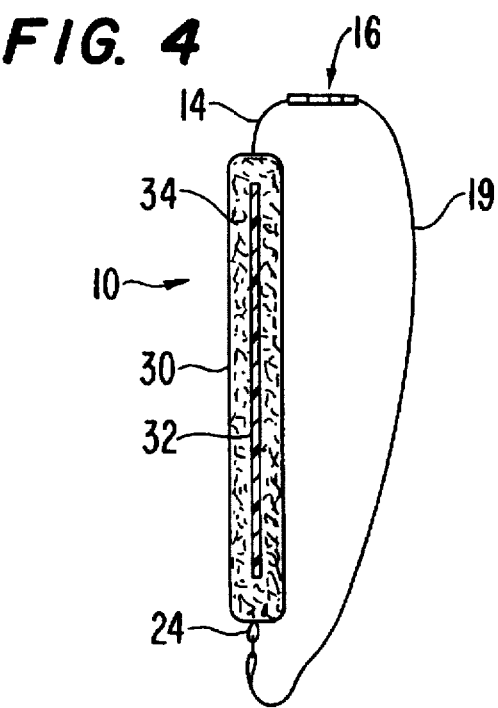
FIG. 4 is a side elevation of the pillow apart from a user.

In use, the pillow is worn in front of the user's chest, generally as shown in FIG. 3. When the user has an urge to cough, the arms can be extended across the front surface of the pillow and used to apply gentle pressure, thereby holding the chest in a position to withstand the forces of the coughing spasm. The location of the pillow permits the user to ride comfortably in a vehicle with diagonal seat belts properly fastened across the front surface of the pillow so that the belt does not rub on any part of the chest and so that the user is cushioned against shocks occasioned by sudden stops or the like. Because the pillow is relatively thin, as compared with its vertical and horizontal dimensions, it is possible to wear the pillow while driving a motor vehicle without discomfort.

While one advantageous embodiment has been chosen to illustrate the invention, it will be understood by those skilled in the art that various modifications can be made therein without departing from the scope of the invention as defined in the appended claims.

What is claimed is:

1. A chest pillow for use by a post-surgical patient comprising a flexible plate having a thickness, a width and a height, said width and height being perpendicular to said thickness and to each other, said width and height approximating upper body width and rib cage height dimensions of a patient;

padding surrounding and covering all sides and edges of said plate;

a fabric cover surrounding and enclosing said padding forming a pillow in which the width and height of said plate within said cover is significantly smaller than a width and height of said padding so that padding is provided between a patient using said pillow and said edges of said plate; and separable strap means extending between upper and lower edges of said pillow, said strap means including first and second straps attached to upper edges of said pillow, third and fourth straps attached to lower edges of said pillow, first and second buckles for detachably joining said first and second straps respectively to said third and fourth straps without said straps crossing each other, said strap means having sufficient length to pass around the shoulders of the patient to support said pillow in a desired position of use wherein the patients arms can be used to hold said pillow against the patient's chest, said straps permitting easy removal from either or both shoulders.

* * * * *